(12) United States Patent
Ehlers et al.

(10) Patent No.: US 6,280,975 B1
(45) Date of Patent: Aug. 28, 2001

(54) IL-6 MUTEIN AND DNA ENCODING THERETO

(75) Inventors: Marc Ehlers; Stefan Rose-John, both of Mainz (DE); Joachim Grotzinger, Bocholtz (NL)

(73) Assignee: Applied Research Systems ARS Holding N.V., Curacao (NL)

( * ) Notice: Subject to any disclaimer, the term of this patent is extended or adjusted under 35 U.S.C. 154(b) by 0 days.

(21) Appl. No.: 09/155,941

(22) PCT Filed: Apr. 9, 1996

(86) PCT No.: PCT/EP96/01506

§ 371 Date: Apr. 6, 1999

§ 102(e) Date: Apr. 6, 1999

(87) PCT Pub. No.: WO97/38103

PCT Pub. Date: Oct. 16, 1997

(51) Int. Cl.[7] ............... C12N 5/10; C12N 15/24; C12N 15/63; C07K 14/54; A61K 38/20
(52) U.S. Cl. ............ 435/69.52; 536/23.1; 536/23.5; 530/351; 435/69.52; 435/71.1; 435/71.2; 435/325; 435/320.1; 435/252.3; 435/254.11; 435/471; 424/85.1; 424/85.2; 514/2; 514/8; 514/12

(58) Field of Search ................... 536/23.1, 23.5; 530/351; 435/69.52, 71.1, 71.2, 325, 320.1, 252.3, 254.11, 471; 514/2, 8, 12; 424/85.1, 85.2

(56) References Cited

PUBLICATIONS

Ehlers et al. J. of Biological Chem. vol. 270, No. 14, pp. 8158–8163, Apr. 7, 1995.
Mikayama et al. Proc. Natl. Acad Sci. USA. vol. 90, pp. 10056–10060, 1993.
Voet et al. Biochemistry. John Wiley & Sons, Inc. pp. 126–128 & 228–234, 1990.
Rieger et al. Glossary of Genetics & Cytogenetics, Fourth Edition, Springer–Verlag, pp, 16–19, 1976.

*Primary Examiner*—Prema Mertz
(74) *Attorney, Agent, or Firm*—Browdy and Neimark

(57) ABSTRACT

The present invention relates to a new IL-6 mutein, a DNA sequence coding for it, its use in therapy as well as a pharmaceutical composition comprising it. It is a potent IL-6 antagonist and can be advantageously used as a medicament in the treatment of diseases in which IL-6 has a pathogenetic action, such as, for example, plasmocytoma/myeloma, osteoporosis and neoplastic and auotoimmune diseases.

8 Claims, 13 Drawing Sheets

B

Figure 1:
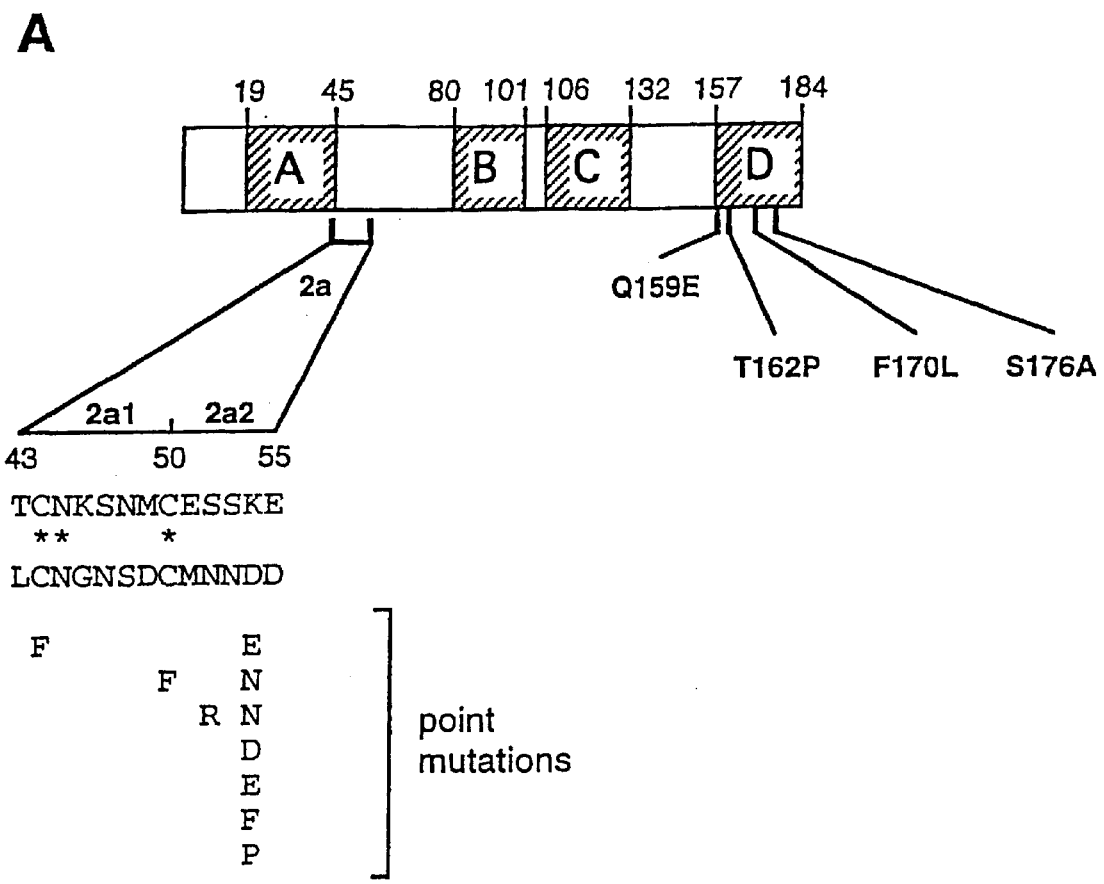
Figure 1:
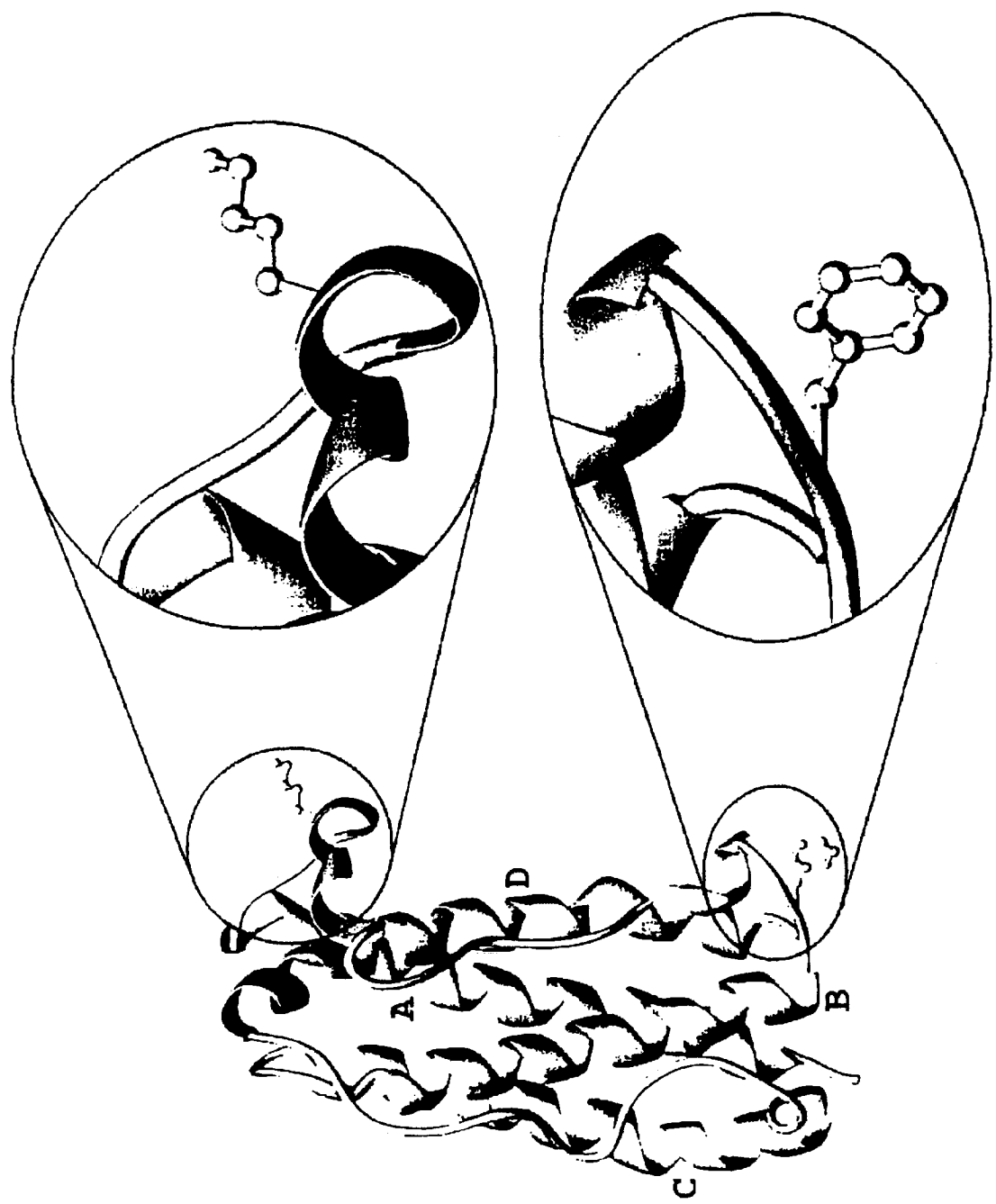

```
43        50   55
TCNKSNMCESSKE    human
MCEKYEKCENSKE    pig
ICEKNDECENSKE    sheep
ICEKNDECESSKE    bovine
MCDNYNKCEDSKE    cat
MCDKFNKCEDSKE    dog
TCNRSNMCDSTKE    cercocebus
TCNRSNMCESSKE    macaque
LCNGNSDCMNNDD    mouse
LCNGNSDCMNSDD    rat
```

FIGURE 1 B

AMINO ACID SEQUENCE OF IL-6 MUTEIN

```
Met Asn Ser Phe Ser Thr Ser Ala Phe Gly Pro Val Ala Phe Ser Leu
Gly Leu Leu Leu Val Leu Pro Ala Ala Phe Pro Ala Pro Val Pro Pro
                                              1
Gly Glu Asp Ser Lys Asp Val Ala Ala Pro His Arg Gln Pro Leu Thr
 5             10                  15                        20
Ser Ser Glu Arg Ile Asp Lys Gln Ile Arg Tyr Ile Leu Asp Gly Ile
             25                      30                     35
Ser Ala Leu Arg Lys Glu Thr Cys Asn Lys Ser Asn Met Cys Glu Ser
             40                  45              50
Ser Pro Glu Ala Leu Ala Glu Asn Asn Leu Asn Leu Pro Lys Met Ala
        55                  60                  65
Glu Lys Asp Gly Cys Phe Gln Ser Gly Phe Asn Glu Glu Thr Cys Leu
    70                  75                  80
Val Lys Ile Ile Thr Gly Leu Leu Glu Phe Glu Val Tyr Leu Glu Tyr
 85             90                      95                  100
Leu Gln Asn Arg Phe Glu Ser Ser Glu Glu Gln Ala Arg Ala Val Gln
                105                 110                     115
Met Ser Thr Lys Val Leu Ile Gln Phe Leu Gln Lys Lys Ala Lys Asn
            120                 125                 130
Leu Asp Ala Ile Thr Thr Pro Asp Pro Thr Thr Asn Ala Ser Leu Leu
        135                 140                 145
Thr Lys Leu Gln Ala Gln Asn Gln Trp Leu Glu Asp Met Pro Thr His
    150                 155                 160
Leu Ile Leu Arg Ser Leu Lys Glu Phe Leu Gln Arg Ser Leu Arg Ala
165                 170                 175                 180
Leu Arg Gln Met
            184
```

FIGURE 2

IL-6 MUTEIN AND DNA ENCODING THERETO

FIELD OF THE INVENTION

The present invention relates to a new IL-6 mutein, a DNA sequence coding for it, its use in therapy as well as a pharmaceutical composition comprising it.

BACKGROUND OF THE INVENTION

Interleukin-6 is released into the plasma upon injury or infection by different cell typs. It is involved in a spectrum of activities like immune defense, hematopoiesis, maturation of megakaryocytes, platelet production and acute phase response (1).

Besides playing a central role in host defense, IL-6 is involved in the pathogenesis of a variety of diseases like plasmocytoma/myeloma, osteoporosis and neoplastic and autoimmune diseases (1).

The IL-6 receptor complex on target cells consists of two different subunits, an 80-kDa specific ligand binding subunit (IL-6Ra) and a 130-kDa signal-transducing protein (gp130) (2–4). IL-6 binds to the IL-6Ra and the complex of IL-6/IL-6Ra becomes associated with a dimer of gp130, thereby initiating the IL-6 signal. IL-6 by itself has no measurable affinity to gp130 (5,6).

Interleukin-6 is a protein characterised by N-terminal heterogeneity. It has been reported (7) as a 184 amino acids (this amino acids numbering will be followed in this patent application). Secondary structure predictions and protein modeling pointed out that IL-6 is a member of the hematopoietic cytokine family characterized by four antiparallel a-helices (A, B, C, and D) (8,9). LIF (leukemia ihibitory factor), CNTF (ciliary neurotrophic factor), IL-11, CT-1 (cardiotrophin-1) and OSM (oncostatin M) also belongs to this family. They all use the gp130 protein in their receptor complex, which explains their overlaping bioactivities (1, 10, 11).

Deletion studies of IL-6 showed that the N-terminal 28 amino acid residuces are dispensable for the biological activity of this molecule. Removal of more than 28 amino acids inactived the protein (12). Further studies predicted that the C-terminus and the end of the A-B loop/beginning of the B-helix (region 2c, residues G77-E95) are involved in the interaction with the IL-6Rα (9, 13–16). These results were corroborated by the recently published human IL-6 model (9) where these two regions were in close proximity.

At present, two interaction sites of IL-6 with gp130 are identified.

i. Epitope mapping of the IL-6 protein with neutralizing mAbs provided evidence that the residues Q152-T162 (beginning of the D-helix) are involved in gp130 interaction (17, 18). Analysis of chimeric human/mouse IL-6 proteins revealed the presence of an epitope within the beginning of the A-B loop of IL-6 which was involved in contacting and activating gp130 (9, 19). Recently, this result was confirmed by demonstrating that leucine 57 is invoved in this interaction (20). This region is in close proximity of the beginning of helix D leading to the assumption that these two regions together form a common interaction site with one gp130 (9, 19, 21).

ii A second interaction site with gp130 was definded in analogy to the GH (growth hormone)/GHR$_2$ complex, the structure of which was solved by X-ray analysis (22). It was speculated, that the parts of the GH important for the interaction with the second GHR are the same in the IL-6 protein important for interaction with one gp130 (23, 24). Indeed, the substitution of two amino acids in the A-helix (Y31D/G35F) and two amino acids in the C-helix (S118R/V121D) also lead to an IL-6 mutant protein with nearly normal affinity to the IL-6Ra, but no bioactivity. These four amino acids seem to be important for the interaction with a second gp130 protein (24, 25).

In view of the previously discussed IL-6 involvement in the pathogenesis of some diseases, the development of inhibitors of IL-6 activity has therefore been the subject of active research. For this purpose, different approaches have been pursued, including the use of antibodies against IL-6, gp130 or gp80; the use of soluble gp130; or the use of muteins for IL-6, or IL-6 Receptor.

The Applicant has investigated the possibility of synthesising new IL-6 muteins that can act as IL-6 receptor antagonists. With this aim, one scientific approach to follow is to synthesise muteins that retain the ability to bind IL-6Rα, but have lost the capacity to recruit gp130. Therefore, the optimal molecule should be the one that does not show IL-6 activity but shows a higher IL-6Rα binding than IL-6 and that contains as few mutations as possible with respect to IL-6, in order to reduce the risks of antigenicity.

DISCLOSURE OF THE INVENTION

The Applicant has now found that by combining point mutations at position 54 with two mutations F170L/S176R, which increase the affinity to the IL-6Ra, and two mutations Q159E/T162P, which decreased the IL-6Ra-dependent interaction with gp130, obtained human IL-6 muteins, which retained receptor binding but failed to activate gp130. In particular, the main object of the present invention is human IL-6 mutein, comprising the amino acid sequence reported in FIG. 2 and in SEQ ID NO:1 as well as fragments thereof. This molecule behaved as efficient IL-6 antagonist on the human IL-6-dependent myeloma cell line XG-1 and shows all the advantages described above.

Another object of the invention is a DNA molecule comprising the DNA sequence coding for the poylpeptide of SEQ ID NO:1, as well as its variants resulting from the degeneracy of the genetic code or point mutations coding for a polypeptide having the same activity as that of SEQ ID NO:1.

A further object of the present invention is a plasmid vector containing the nucleotide sequence of the invention.

In a further aspect, the present invention provides the use of the protein as a medicament. In particular, it relates to the use of the protein of the invention in the manufacture of a medicament for the treatment of diseases in which IL-6 has a pathogenetic action, such as, for example, plasmocytoma/myeloma, osteoporosis and neoplastic and auotoimmune diseases.

The medicament is preferably presented in the form of a pharmaceutical composition comprising the protein of the invention together with one or more pharmaceutically acceptable carriers and/or excipients. Such pharmaceutical compositions form yet a further aspect of the present invention.

One method for preparing the mutein of the invention is by way of PCR technology using synthetic oligonucleotides, which contain a mismatch at the base that one wants to mutate, as primers.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example, the DNA molecule coding for the polypeptide of the invention are inserted into appropriately constructed expression vectors by techniques well known in the art (see Sambrook et al, 1989). Double stranded cDNA is linked to plasmid vectors by homopolymeric tailing or by restriction linking involving the use of synthetic DNA linkers or blunt-ended ligation techniques: DNA ligases are used to ligate the DNA molecules and undesirable joining is avoided by treatment with alkaline phosphatase.

In order to be capable of expressing the desired protein, an expression vector should comprise also specific nucleotide sequences containing transcriptional and translational regulatory information linked to the DNA coding the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the polypeptide of the invention is inserted into vector(s), having the operably linked transcriptional and translational regulatory signals, which is capable of integrating the desired gene sequences into the host cell. The cells which have been stably transformed by the introduced DNA can be selected by also introducing one or more markers which allow for selection of host cells which contain the expression vector. The marker may also provide for phototrophy to a auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Factors of importance in selecting a particular plasmid or viral vector include: the ease with which recipient cells, that contain the vector may be recognized and selected form those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese hamster ovary (CHO) cells, because they provide post-translational modifications to protein molecules, including correct folding or glycosylation at correct sites. Also yeast cells can carry out post-translational peptide modifications including glycosylation.

A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired protein.

Purification of the recombinant proteins is carried out by any one of the methods known for this purpose, ie. any conventional procedure involving extraction, precipitation, chromatography, electrophoresis, or the like. A further purification procedure that may be used in preference for purifying the protein of the invention is affinity chromatography using monoclonal antibodies which bind the target protein and which are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

The invention will now be described by means of the following Example, which should not be construed as in any way limiting the present invention. The Example will refer to the Figures specified here below.

BRIEF DECRIPTION OF THE DRAWINGS

FIGS. 1A, 1B, 1C. Point mutants of human IL-6 protein. (A) representation of the human IL-6 protein with the four predicted a-helices shown as hatched boxes. Numbers indicate the predicted first and last residues of the a-helices. The amino acid sequences of regions 2c and 2a with its subdivision into region 2a1 and 2a2 of human (top) (SEQ ID NO:14) and murine (bottom) (SEQ ID NO:15) IL-6 are shown. The produced point mutations in the region 2a are presented. (B) alignment of the IL-6 species (SEQ ID NOS:14–23) in the region 2a. (C) ribbon representation of the human IL-6 model. Representation of F78 (bottom) important for IL-6Ra binding and K54 (top) important for IL-6Ra-dependent gp130 interaction The N-terminus corresponds to residue 17 of human IL-6 (Ehlers et al. 1994).

FIG. 2. Amino sequence of the human IL-6 mutein of the present invention. It contains five point mutations with respect to the human IL-6, at positions 54, 159, 162, 170, 176. Such positions are reported in bold.

FIGS. 3A, 3B, 3C, 3D. Binding and bioactivity of K54 point mutants of human IL-6. (A) binding of the IL-6 muteins to soluble human IL-6Ra. Average values of two experimentes are shown. (B) proliferation of murine B9 cells and (C) of human XG-1 cells in response to IL-6 mutants. One representative of three experiments is shown. (D) induction of haptoglobin expression in human hepatoma cells by IL-6 muteins. The amount of human IL-6 needed for 50% haptoglobin expression was set as 100%. Average values of two experiments are shown.

FIGS. 4A, 4B, 4C, 4D. Binding and bioactivity of point mutations of K54 in combination with EP-LR. (A) binding of the IL-6 muteins to soluble human IL-6Ra. Average values of two experimentes are shown. (B) proliferation of murine B9 cells and (C) of human XG-1 cells in response to IL-6 mutants. One representative of three experiments is shown. (D) induction of haptoglobin expression in human hepatoma cells by IL-6 muteins. The amount of haptoglobin expression in the presence of 1 $\mu$g/ml mutant is shown. Average values of two experiments are shown.

Figure 5:
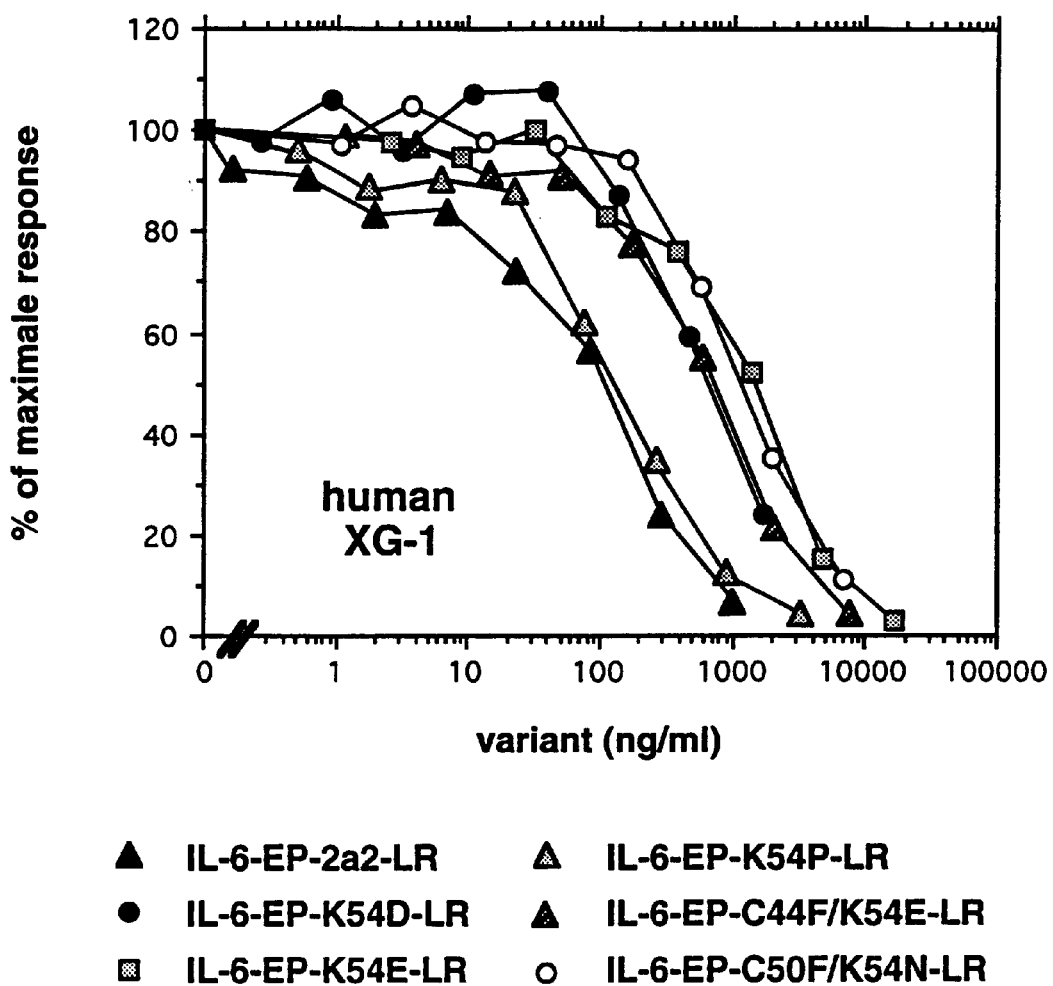

FIG. 5. Antagonistic effect of point mutations of K54 in combination with EP-LR on the human IL-6-induced proliferation of XG-1 cells. The indicated concentrations of the IL-6 mutants were added to XG-1 cells in the presence of 100 pg/ml human IL-6 and proliferation was measured. Average values of four experiments are shown.

EXAMPLES

Materials and Methods

Chemicals

Restriction enzymes AccI, EcoNI, HindIII, NcoI, NheI, and XbaI were obtained from AGS (Heidelberg, Germany), polynucleotide kinase, calf intestinal phosphatase and T4 DNA ligase were from Boehringer Mannheim (Mannheim, Germany). Restriction enzyme BspEI and Vent DNA polymerase were purchased from NEN Biolabs (Schwalbach, Germany) and cell culture media from Gibco (Eggenstein, Germany). Bolton-Hunter reagent (74 TBq/mmol) and tran [$^{35}$S]label were obtained from Amersham International (Amersham, United Kingdom).

Oligonucleotides were obtained from Pharmacia (Freiburg, Germany).

Goat and rabbit polyclonal serum anti-human haptoglobin were purchased from Sigma (Deisenhofen, Germany) and alkaline phosphatase-conjugated donkey polyclonal serum anti-rabbit IgG from Pierce (Rockford, U.S.A.).

Human IL-6 cDNA was a gift of Drs. T. Hirano and T. Kishimoto (Osaka, Japan).

The bacterial expression plasmid pRSET 5d and the host bacteria BL21(DE3) were described by Schöpfer et al., (26). After replacing the signal sequences by a translational start codon, the cDNA coding for human IL-6 was cloned into the vector pRSET 5d using the restriction sites NcoI and HindIII (27).

The human myeloma cell line XG-I was generously supplied by Dr. B. Klein (Nantes, France).

The soluble IL-6Ra protein was expressed in E. coli, renatured and purified (28).

The polyclonal monospecific antiserum against the IL-6Ra was prepared by injecting a part of the extracellular domain of the soluble IL6Ra protein into rabbits (28).

Construction of Expression Vectors

To introduce point mutations at amino acid 54 into the human IL-6 (pRSET 5d-huIL-6-K54X), four oligonucleotides were fused and ligated into the EcoNI-NheI-digested pRSET 5d-mutant 2a (9). The oligonucleotides were:

```
5' AAC ATG TGT GAA AGC AGC GAT GAG GCG 3' sense (54D) (SEQ ID NO: 2)
5' CTA GCG CCT CATCGC TGC TTT CAC AC 3'  antisense (K54D) (SEQ ID NO: 3)
5' AAC ATG TGT GAA AGC AGC GAA GAG GCG 3' sense (K54E) (SEQ ID NO: 4)
5' CTA GCG CCT CTTCGC TGC TTT CAC AC 3'  antisense (K54E) (SEQ ID NO: 5)
5' AAC ATG TGT GAA AGC AGC TTT GAG GCG 3' sense (K54F) (SEQ ID NO: 6)
5' CTA GCG CCT CAAAGC TGC TTT CAC AC 3'  antisense (K54F) (SEQ ID NO: 7)
5' AAC ATG TGT GAA AGC AGC AAT GAG GCG 3' sense (K54N) (SEQ D NO: 8)
5' CTA GCG CCT CATTGC TGC TTT CAC AC 3'  antisense (K54N) (SEQ ID NO: 9)
5' AAC ATG TGT GAA AGC AGC CCC GAG GCG 3' sense (K54P) (SEQ D NO: 10)
5' CTA GCG CCT CGGGGC TGC TTT CAC AC 3'  antisense (K54P) (SEQ D NO: 11)
5' GAA AGG AGA CAT GTA ACA AGA GT 3'     sense (SEQ ID NO: 12)
5' ATG TrA CTC TTG TTA CAT GTC TCC TTT 3' antisense (SEQ ID NO: 13)
```

To combine the point mutations of amino acid 54 with the two point mutations F170L/S176R (short designation, LR) and the two point mutations Q159E/T162P (short designation, EP), the vectors pRSET 6d-huIL-6-EP-K54X-LR were constructed by ligating NcoI-XbaI cDNA fragments from pRSET-5d-huIL-6-K54X into NcoI-XbaI-digested vector pRSET 6d-huIL-6-Q159E/T162P-2a2-F170L/S176R (short designation, pRSET 6d-huIL-6-EP-2a2-LR) (19). The integrity of all constructs was verified by restriction fragment analysis and DNA sequencing (29).

Preparation of Proteins

BL21(DE3) bacteria were transformed with the appropriate pRSET expression vectors. Gene expression and refolding of proteins solubilized from inclusion bodies was carried out as described (27, 30, 31). Refolded proteins were purified to >90% homogeneity. The puritiy of the recombinant proteins was checked by 12.5% SDS-PAGE and silverstaining.

Binding of IL-6 to the Soluble Human IL-6Ra

Purified IL-6 mutant proteins were serially diluted in PBS containing 0.02% TWEEN 20/0.2% BSA and added to 1 ng human $^{125}$I-IL6 (60,000–90,000 cpm/ng) and 1.7 ng soluble human IL-6Ra expressed in E. coli (28) to a final volume of 500 µl. After overnight incubation at 4° C. IL-6/sIL-6Ra-complexes were immunoprecipitated using an IL-6Ra antiserum and protein A Sepharose, and radioactivity was determined by g-counting.

Biological Assays

For the murine B9 and the human XG-I proliferation assays, IL-6 mutant proteins were serially diluted to concentrations indicated in the figures. The assays were performed as described (32, 33). One B9 unit corresponding approximately to 1 pg human IL-6 per ml, lead to half maximal proliferation of B9 cells. With human XG-1 cells half maximal proliferation was obtained after stimulation with about 50 pg/ml human IL-6. For the acute phase protein secretion assay, human hepatoma cells (Hep3B) were cultured in Dulbecco's modified Eagle's medium (DMEM) with 10% fetal calf serum, plated in 96-well cell culture plates and left to reach confluence. Cells were washed with PBS, starved for 1 h in DMEM without fetal calf serum, and subsequently treated for 20 h in 100 ml of serum-free DMEM with increasing amounts of IL-6 muteins. The amount of haptoglobin secreted in the culture medium was detected by an enzyme-linked immunosorbent assay (34).

Results

Amino Acid K54 of IL-6 is Involved in the IL-6Ra-dependent gp130 Interaction

Studies with human/murine IL-6 chimeric proteins had pointed out that region 2a2 (residues 50–55) of IL-6 protein is important for the IL-6Ra-dependent interaction with gp130 (19) (FIG. 1A). The exchange of these residues against the corresponding murine amino acids resulted in decreased binding to gp130 and 30-fold decreased bioactivity on human XG-1 cells. The alignment of ten IL-6 species revealed that within the 2a2 region the positively charged K54 is conserved in 8 species but is changed into the negatively charged asparagine acid in the murine and rat sequence (35, 36) (FIG. 1B). We therefore exchanged K54 (FIG. 1C) for the amino acids indicated in FIG. 1A. The cloning procedure yielded also three double point mutations of IL-6: C44F/K54E, C50F/K54N and S52R/K54N, which were also analyzed (FIG. 1A).

Figure 3:
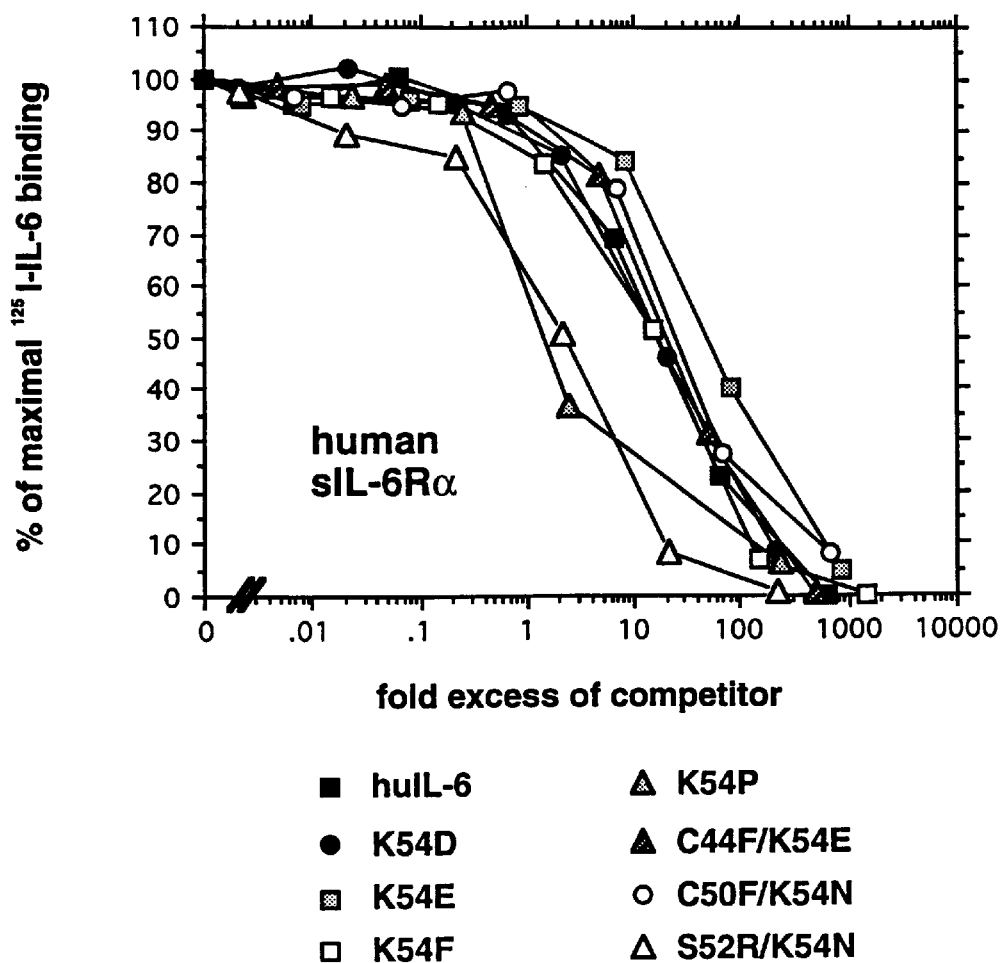
Figure 3:
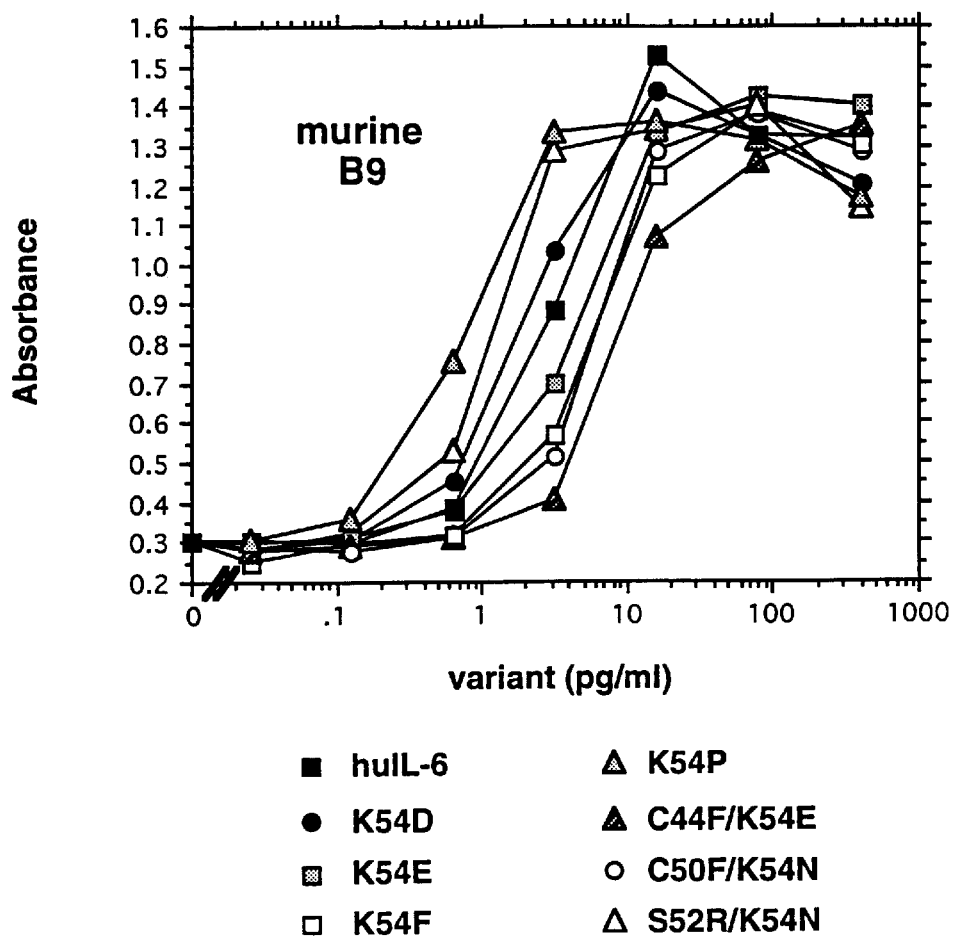
Figure 3:
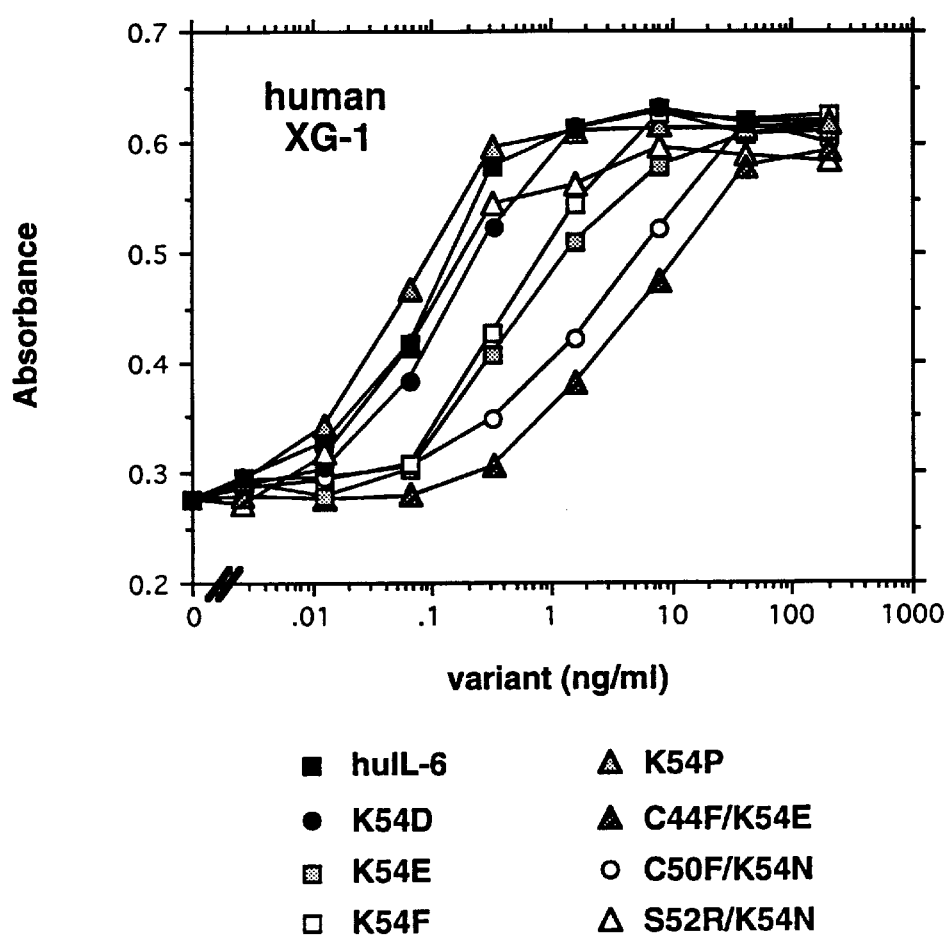
Figure 3:
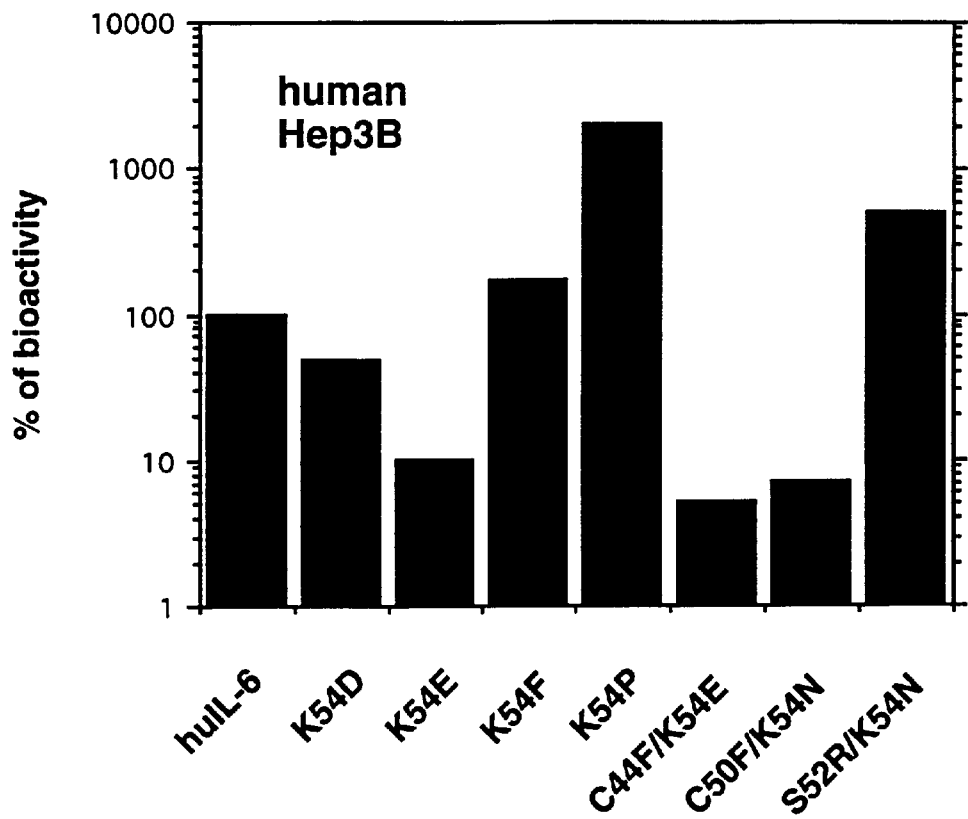
Figure 4:
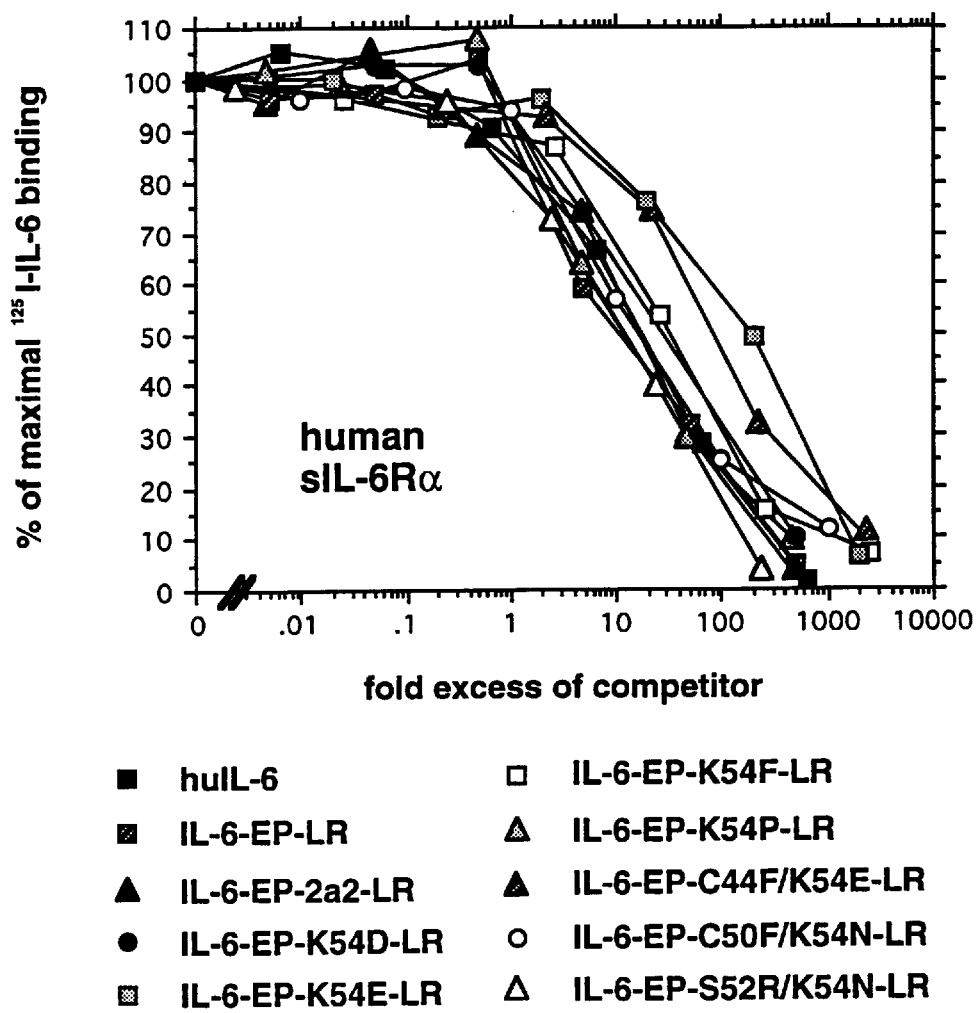
Figure 4:
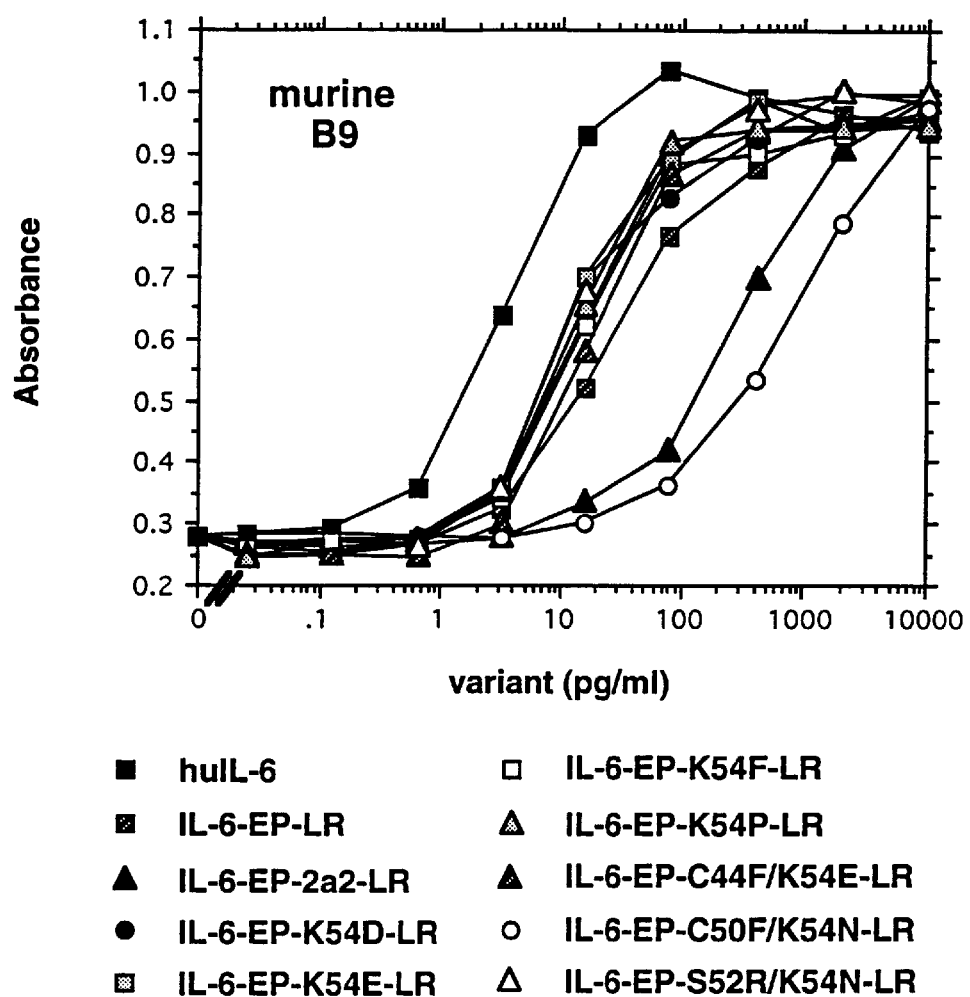
Figure 4:
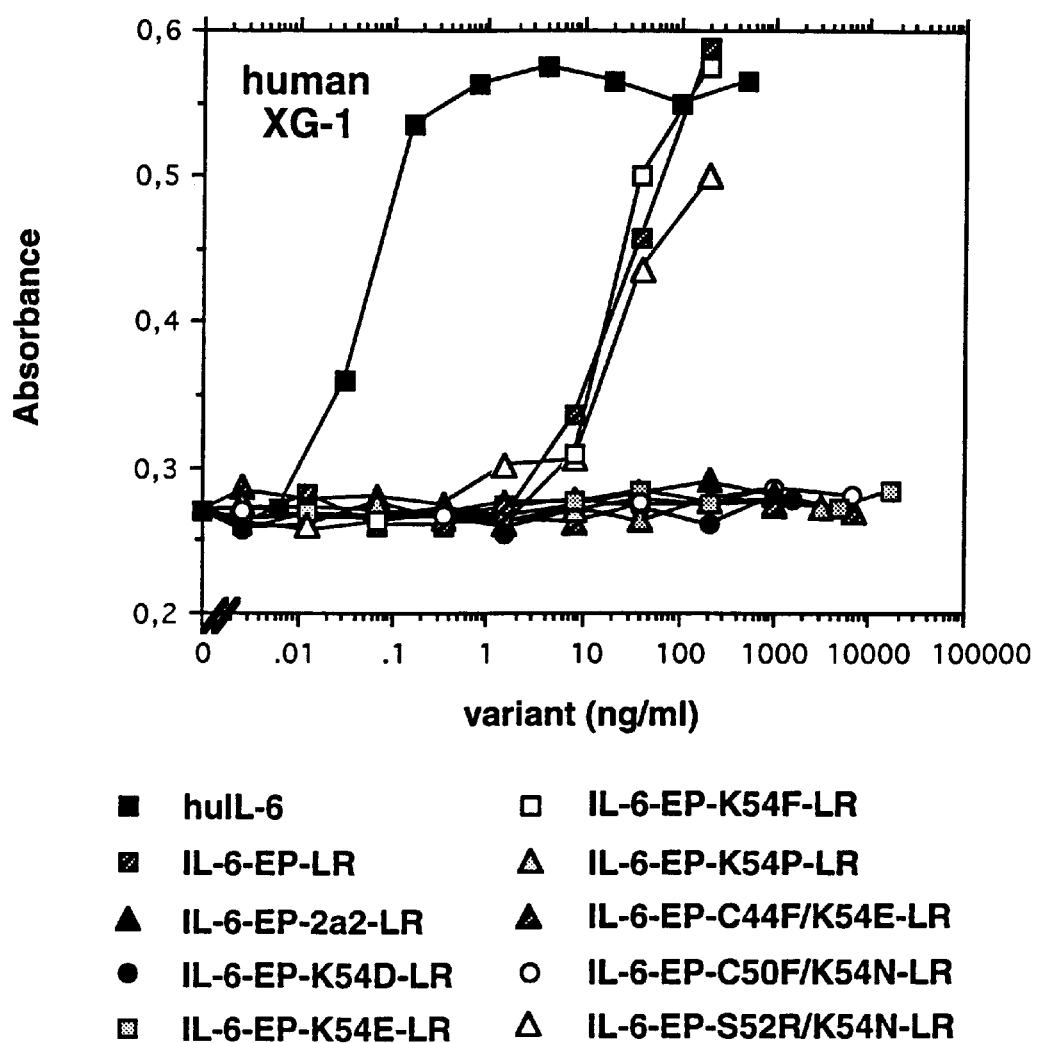
Figure 4:
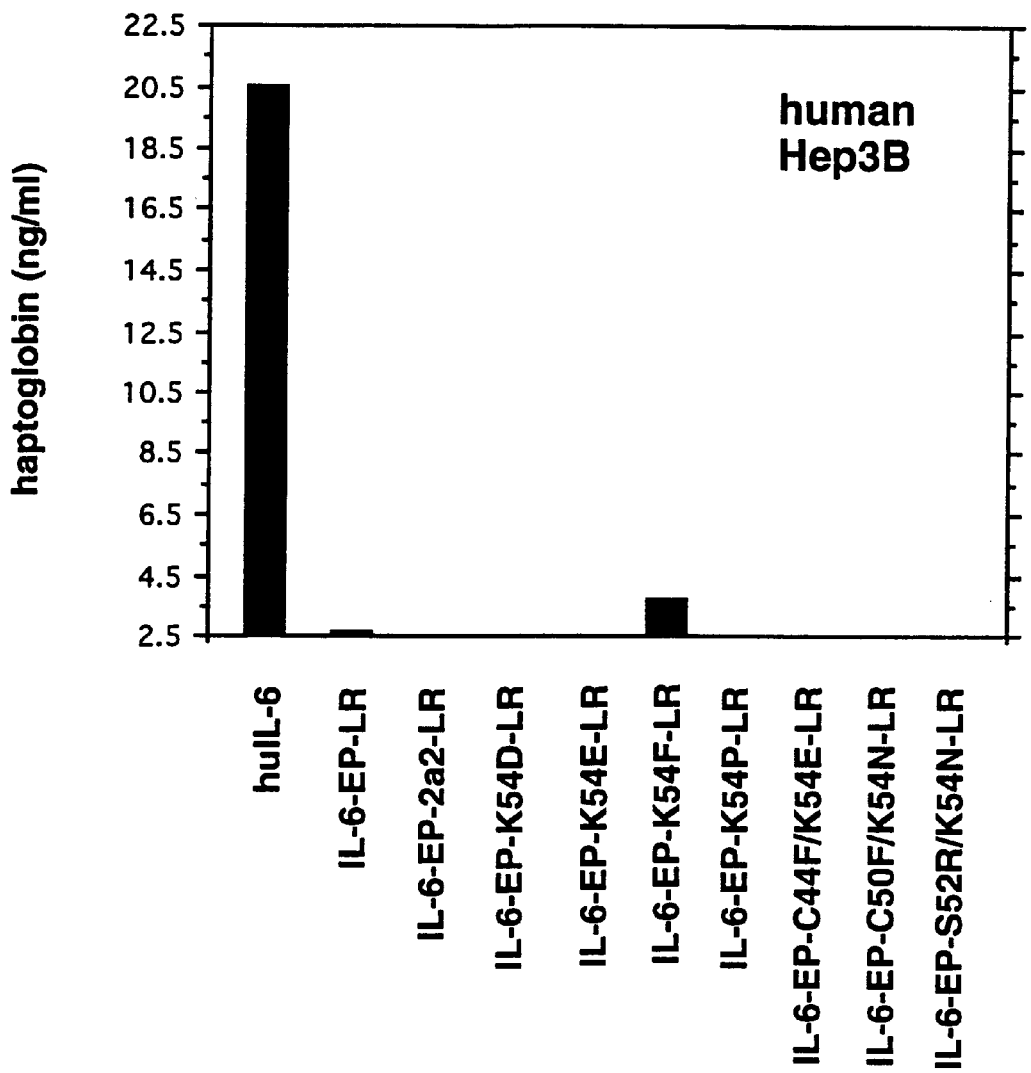

To examine the influence of K54 point mutations to the IL-6Ra-dependent gp130 interaction, we first measured binding to the IL-6Ra by displacement of human $^{125}$I-IL-6 binding to a soluble form of the IL-6Ra protein by an excess of the point mutants. As shown in FIG. 3A, unlabeled human wild typ IL-6 displaced human $^{125}$I-IL-6 binding to 50% when used in a 10–20-fold molar excess. The point mutant K54P and the double mutant S52R/K54N showed a 10-fold higher affinity as human IL-6, whereas the mutant K54E had a 3-fold lower affinity as huIL-6 to the IL-6Ra. The other examined mutants showed a similar affinity as human IL-6. Again the mutants stimulated the proliferation of murine IL-6-dependent B9 cells to a similar extent as human IL-6, which demonstrated that their structures were intact (FIG. 3B).

On human myeloma XG-1 cells and on human hepatoma cells the bioactivity pattern of the IL-6 muteins was: K54P>S52R/K54N>huIL-6=K54F>K54D>K54E>C50F/K54N>C44F/K54E. Thus, mutants K54P and S52R/K54N having the highest affinity to the IL-6Ra also showed the highest bioactivity on human cells. The exchange of the positively charged lysine 54 against the corresponding negatively charged asparagine acid resulted only in a slightly reduced bioactivity on human cells whereas the exchange against Glu resulted in a substantial reduction (10-fold) of bioactivity.

Design of New Human IL-6 Receptor Antagonists

Recently, we have shown that the introduction of the murine residues 50–55 (region 2a2) and of the two point mutations F170L/S176R (short designation, LR) which increase the affinity to the IL-6Ra, into the double mutant Q159E/T162P (short designation, IL-6-EP) which show decreased interaction with gp130, resulted in an IL-6 mutein with no detectable bioactivity on human cells (19). The affinity of this IL-6 mutant (IL-6-EP-2a2-LR) to the human IL-6Ra was similar to human IL-6. This IL-6 mutant was an effective IL-6 receptor antagonist on the highly sensitive human IL-6-dependent human myeloma cell line XG-1.

We introduced the K54 mutants into the mutant IL-6-EP-LR. The resulting IL-6 mutant proteins were called IL-6-EP-K54X-LR where X designates all mutations introduced at position 54 (FIG. 1A). Mutant IL-6-EP-C44F/K54E-LR and mutant IL-6-EP-K54E-LR showed a reduced affinity to the human IL-6Ra whereas all other mutants behaved like human IL-6 (FIG. 4A). Proliferation of murine B9 cells was strongly reduced for mutant IL-6-EP-2a2-LR and IL-6-EP-S52R/K54N-LR. All other mutants were about 5–10-fold less active than human IL-6 (FIG. 4B). In contrast, proliferation of human myeloma XG-1 cells was reduced by about three orders of magnitude for the mutants IL-6-EP-LR, IL-6-EP-K54F-LR and IL-6-EP-S52R/K54N-LR (FIG. 4C). All other mutants showed no detectable bioactivity. On human Hep3B cells only the mutants IL-6-EP-LR and IL-6-EP-K54F-LR showed residual activity (FIG. 4D).

When mutants without bioactivity were added at increasing amounts to human myeloma cells (XG-1) which were stimulated by 100 pg/ml human IL-6, an inhibition of proliferation was observed. FIG. 5 shows that addition of the mutants IL-6-EP-2a2-LR and IL-6-EP-K54P-LR led to 50% inhibition of proliferation at about 100 ng/ml whereas all other mutants were about 5–10 times less effective.

Discussion

Amino Acid K54 is Part of a gp130 Binding Epitope

All IL-6 muteins with a replacement of K54 by various amino acid residues bind efficiently to the human IL-6Ra. Interestingly, the introduction of P54 and the double mutation S52R/K54N results in IL-6 proteins with higher affinity to the human IL-6Ra. Since the 2a2 region which includes residue 54 is involved in gp130 interaction (19), this is most likely an indirect effect. We speculate that the presence of P54 or the charged amino acid arginine in position 52 leads to a relocation of the loop between helix A and helix B thereby changing the position of region 2C which is directly involved in IL-6Ra interaction. The replacement of the lysine 54 which is conserved within eight species by an asparagine acid which is conserved in mouse and rat leads to a slightly reduced bioactivity whereas the replacement by gluthamine acid leads to a substantial reduction (10-fold) of bioactivity. Since gluthamine acid carries a side chain which is by one methylengroup longer than that of asparagine acid, it is likely that the distance between the charged group and the human IL-6Ra is critical. From these data it can be hypothesized that K54 makes contact to a negatively charged residue of human gp130 and that the introduction of a negative charged amino acid at position 54 in human IL-6 leads to a reduction of recognition between gp130 and the IL-6/IL-6Ra complex. The mutation of the cysteins 44 or 50 resulted in IL-6 muteins with only slightly reduced bioactivity confirming the recent results by Rock et al. (34) who could show that the substitution of the cysteins 44 and 50 did not result in inactive IL-6 muteins.

Ligand Receptor Interaction

The structure of the human growth hormone/growth hormone receptor complex ($GH/GHR_2$) has been solved (22). The interaction sites between growth hormone and its receptor have been extensively mutated (38–40) and the contribution of single amino acid residues to the binding energy has been evaluated (41). Since the growth hormone receptor complex is so far the only receptor-ligand pair of the hematopoietic cytokine family which is understood at the atomic level, it has served as a paradigm for other members of this family. For the growth hormone receptor complex it has been shown that the interacting epitope on both, ligand and receptor side consists of about 30 amino acid residues (41). The contribution of these amino acid residues, however, is unequal. Most of the binding energy is provided by two hydrophobic interactions. This binding core is surrounded by less important contact residues that are generally hydrophilic and partially hydrated, of which only one third contribute to the binding energy. It has been postulated that such a set-up of the binding site is also applicable to other ligand-receptor interactions (41).

K54, however, is believed to be one of the surrounding residues of a central IL-6/gp130 interaction area which therefore contributes to a small extent to the binding energy. The relatively strong effect of the K54P substitution in the antagonistic IL-6 mutein is attributed to structural changes in the AB-loop.

IL-6 Receptor Antagonists

So far two major regions of IL-6 have been identified which are believed to contact gp130, (i) the 2a2 region (residues 50–55) and leucine 57 which are complemented by the top of the helix D of IL-6 and (ii) an epitope which is formed by parts of helix A and helix C (9, 18–21, 23, 24). Binding of IL-6 to the IL-6Ra requires the end of the A-B loop (residue 78) as well as the C-terminus of the protein (9, 13–16). It is clear that two gp130 molecules are necessary for signal initiation and it is very likely that the role of the two gp130 interaction sites within IL-6 is to engage the two gp130 proteins. Alterations within both gp130 interacting regions have led to molecules which retained their receptor binding capacity but failed to initiate signaling. It has been shown that such molecules can be used as IL-6 receptor antagonists (19, 21, 23, 24). The fact that simultaneously improving the IL-6Ra binding characteristics of IL-6 muteins has led to so-called superantagonists (19, 21, 24) suggesting that it is possible to change binding properties to various receptor subunits in a somehow independent fashion.

The new IL-6 receptor antagonist which is presented in this patent application contains a single K54P substitution within the 2a2 region and is still as effective as the recently established IL-6 mutein with 5 amino acid exchanges in the 2a2 region (19).

Interestingly, the K54P mutant protein showed higher IL-6Ra binding than human IL6 whereas the combination mutant with EP and LR exhibited normal IL-6Ra binding.

Concerning the therapeutic potential of cytokine receptor antagonists it is clear that the fewer amino acids are exchanged the smaller is the chance that the antagonist will be antigenic. In this respect the IL-6 mutein IL-6-EP-K54P-LR is an improvement of IL-6 receptor antagonists available so far.

References

1. Akira, S et al., Adv. Immunol. 54:1, 1993.
2. Yamasaki K. et al., Science 241:825, 1988.
3. Taga, T. et al., Cell 58:573, 1989.
4. Hibi M et al., Cell 63:1149, 1990.
5. Zohlnhöfer, D. et al., FEBS Lett. 306:219, 1992.
6. Murakami, M et al., Science 260:1808, 1993.
7. Hirano, T. et al. Nature 324:73, 1986.
8. Bazan, J. F., Immunol. Today 11:350, 1990.
9. Ehlers, M., J. Immunol. 153:1744, 1994.
10. Pennica, D. et al., Proc. Nat. Acad. Sci. U.S.A. 92:1142, 1995.
11. Pennica, D. et al., J. Biol. Chem. 270:10915, 1995.
12. Brakenhoff, J. P. J. et al., J. Immunol. 143:1 175. 1989.
13. Krüttgen, A. et al., FEBS Lett. 262:323, 1990.
14. Krüttgen, A., et al., FEBS Lett. 273:95, 1990.
15. Lütticken, C. et al., FEBS Lett. 282:265, 1991.
16. Leebeck, F. W. G et al., J. Biol. Chem. 267:14832, 1992.
17. Brakenhoff J. P. J, Serono Symp. Pub. Raven Press. 88:33, 1992.
18. Brakenhoff J. P. J., J. Biol. Chem 269:86, 1994.
19. Ehlers, M. et al., J. Biol. Chem. 270:8158, 1995.
20. De Hon, F. D. et al., FEBS Lett. 369:187, 1995.
21. De Hon, F. D. et al., J. Exp. Med. 180:2395, 1994.
22. De Vos, A. M. et al., Science 255:306, 1992.
23. Savino, R. et al., EMBO J. 13:281, 1994.
24. Savino, R et al., EMBO J. 13:5863, 1994.
25. Paonessa, G. et al., EMBO J. 14:1942, 1995.
26. Schoepfer, R. et al., Neuron 5:393, 1990.
27. Van Dam, M. et al., J. Biol. Chem. 268:15285, 1992.
28. Stoyan, T., Eur. J. Biochem. 216:239, 1993.
29. Sanger, F. et al, Proc. Natl. Acad. Sci. U.S.A. 74:5463, 1977.
30. Studier, F. W. et al., Meth. Enzymol. 185:60, 1990.
31. Arcone, R. et al., Eur. J. Biochem. 198:541, 1991.
32. Aarden, L. A et al., Eur. J. Immunl. 17:1411, 1987.
33. Zhang, X.-G. et al., Blood 76:2599, 1990.
34. Salvati A. L. et al., J. Biol. Chem. 270:12242, 1995.
35. Van Snick, J. et al., Eur. J. Immunol. 18:193, 1988.
36. Northemann, W. et al., J. Biol. Chem. 264:16072, 1989.
37. Rock, F. L. et al., Biochem. 33:5146, 1994.
38. Cunningham, B. C. et al., Science 244:1081, 1989.
39. Cunningham, B. C. et al., J. Mol. Biol. 234:554, 1993.
40. Bass, S. H et al., Proc. Natl. Acad. Sci. U.S.A. 88:4498, 1991.
41. Clackson T., et al., Science 267:383, 1995.

What is claimed is:

1. A polypeptide comprising the amino acid sequence of SEQ ID NO:1.

2. A DNA molecule comprising the DNA sequence coding for the polypeptide of claim 1.

3. A vector comprising the DNA sequence of claim 2.

4. A host cell transformed with the DNA sequence of claim 2.

5. A process for producing a polypeptide, comprising:
   (a) culturing the host cells of claim 4 in a suitable culture medium; and
   (b) isolating said polypeptide from the culture medium.

6. A composition comprising a polypeptide in accordance with claim 1, together with one or more pharmaceutically acceptable carriers and/or excipients.

7. A host cell transformed with the vector of claim 3.

8. A method for inhibiting the binding of IL-6 with the IL-6 receptor comprising administering an effective amount of a polypeptide in accordance with claim 1.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 212 amino acids
      (B) TYPE: amino acid
      (C) STRANDEDNESS: <Unknown>
      (D) TOPOLOGY: linear (ii) MOLECULE TYPE: peptide (iii) HYPOTHETICAL: NO (iv) ANTI-SENSE: NO (v) FRAGMENT TYPE: N-terminal

```
    (ix) FEATURE:
         (A) NAME/KEY: Protein
         (B) LOCATION:1..184

(xi) SEQUENCE DESCRIPTION: SEQ ID NO: 1:

Met Asn Ser Phe Ser Thr Ser Ala Phe Gly Pro Val Ala Phe Ser Leu
            -25                 -20                 -15
Gly Leu Leu Leu Val Leu Pro Ala Ala Phe Pro Ala Pro Val Pro Pro
            -10                  -5                   1
Gly Glu Asp Ser Lys Asp Val Ala Ala Pro His Arg Gln Pro Leu Thr
  5                  10                  15                  20
Ser Ser Glu Arg Ile Asp Lys Gln Ile Arg Tyr Ile Leu Asp Gly Ile
             25                  30                  35
Ser Ala Leu Arg Lys Glu Thr Cys Asn Lys Ser Asn Met Cys Glu Ser
             40                  45                  50
Ser Pro Glu Ala Leu Ala Glu Asn Asn Leu Asn Leu Pro Lys Met Ala
             55                  60                  65
Glu Lys Asp Gly Cys Phe Gln Ser Gly Phe Asn Glu Glu Thr Cys Leu
 70                  75                  80
Val Lys Ile Ile Thr Gly Leu Leu Glu Phe Glu Val Tyr Leu Glu Tyr
 85                  90                  95                 100
Leu Gln Asn Arg Phe Glu Ser Ser Glu Glu Gln Ala Arg Ala Val Gln
            105                 110                 115
Met Ser Thr Lys Val Leu Ile Gln Phe Leu Gln Lys Lys Ala Lys Asn
            120                 125                 130
Leu Asp Ala Ile Thr Thr Pro Asp Pro Thr Thr Asn Ala Ser Leu Leu
            135                 140                 145
Thr Lys Leu Gln Ala Gln Asn Gln Trp Leu Glu Asp Met Pro Thr His
            150                 155                 160
Leu Ile Leu Arg Ser Leu Lys Glu Phe Leu Gln Arg Ser Leu Arg Ala
165                 170                 175                 180
Leu Arg Gln Met (2) INFORMATION FOR SEQ ID NO: 2:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 2:

AACATGTGTG AAAGCAGCGA TGAGGCG                                        27

(2) INFORMATION FOR SEQ ID NO: 3:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (xi) SEQUENCE DESCRIPTION: SEQ ID NO: 3:
```

CTAGCGCCTC ATCGCTGCTT TCACAC                                    26

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 4:

AACATGTGTG AAAGCAGCGA AGAGGCG                                   27

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 5:

CTAGCGCCTC TTCGCTGCTT TCACAC                                    26

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 6:

AACATGTGTG AAAGCAGCTT TGAGGCG                                   27

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 7:

CTAGCGCCTC AAAGCTGCTT TCACAC                                    26

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 8:

AACATGTGTG AAAGCAGCAA TGAGGCG                                            27

(2) INFORMATION FOR SEQ ID NO: 9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 9:

CTAGCGCCTC ATTGCTGCTT TCACAC                                             26

(2) INFORMATION FOR SEQ ID NO: 10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 10:

AACATGTGTG AAAGCAGCCC CGAGGCG                                            27

(2) INFORMATION FOR SEQ ID NO: 11:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 11:

CTAGCGCCTC GGGGCTGCTT TCACAC                                             26

(2) INFORMATION FOR SEQ ID NO: 12:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 12:

GAAAGGAGAC ATGTAACAAG AGT                                                23

(2) INFORMATION FOR SEQ ID NO: 13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 13:

ATGTTACTCT TGTTACATGT CTCCTTT                                              27

(2) INFORMATION FOR SEQ ID NO: 14:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 14:

Thr Cys Asn Lys Ser Asn Met Cys Glu Ser Ser Lys Glu
                 5                  10

(2) INFORMATION FOR SEQ ID NO: 15:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 15:

Leu Cys Asn Gly Asn Ser Asp Cys Met Asn Asn Asp Asp
                 5                  10

(2) INFORMATION FOR SEQ ID NO: 16:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 16:

Met Cys Glu Lys Tyr Glu Lys Cys Glu Asn Ser Lys Glu
                 5                  10

(2) INFORMATION FOR SEQ ID NO: 17:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 17:

Ile Cys Glu Lys Asn Asp Glu Cys Glu Asn Ser Lys Glu
                 5                  10

(2) INFORMATION FOR SEQ ID NO: 18:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

Ile Cys Glu Lys Asn Asp Glu Cys Glu Ser Ser Lys Glu
                 5                  10

(2) INFORMATION FOR SEQ ID NO: 19:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

Met Cys Asp Asn Tyr Asn Lys Cys Glu Asp Ser Lys Glu
                 5                  10

(2) INFORMATION FOR SEQ ID NO: 20:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 20:

Met Cys Asp Lys Phe Asn Lys Cys Glu Asp Ser Lys Glu
                 5                  10

(2) INFORMATION FOR SEQ ID NO: 21:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

Thr Cys Asn Arg Ser Asn Met Cys Asp Ser Thr Lys Glu
                 5                  10

(2) INFORMATION FOR SEQ ID NO: 22:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

Thr Cys Asn Arg Ser Asn Met Cys Glu Ser Ser Lys Glu
                 5                  10

```
(2) INFORMATION FOR SEQ ID NO: 23:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

Leu Cys Asn Gly Asn Ser Asp Cys Met Asn Ser Asp Asp
                 5                  10
```